United States Patent
Chen et al.

(10) Patent No.: US 7,955,389 B2
(45) Date of Patent: Jun. 7, 2011

(54) ARTIFICIAL SPHINCTER SYSTEM

(75) Inventors: Wen-Shiang Chen, Taipei (TW);
Hao-Li Liu, Tao-Yuan County (TW);
Yen-Tung Huang, Taipei County (TW);
Chien-Ching Ma, Taipei (TW);
Wei-Bor Tsai, Taipei (TW); Wen-Pin Shih, Taipei (TW); Chi-An Dai, Taipei (TW)

(73) Assignee: National Taiwan University, Taipei (TW)

( * ) Notice: Subject to any disclaimer, the term of this patent is extended or adjusted under 35 U.S.C. 154(b) by 204 days.

(21) Appl. No.: 12/140,943

(22) Filed: Jun. 17, 2008

(65) Prior Publication Data

US 2009/0248151 A1 Oct. 1, 2009

(30) Foreign Application Priority Data

Mar. 31, 2008 (TW) .............................. 97111669 A

(51) Int. Cl.
*A61F 2/08* (2006.01)
(52) U.S. Cl. ...................................... 623/14.13; 623/4.1
(58) Field of Classification Search ................... 623/4.1, 623/5.11–5.13, 6.17, 6.36, 6.41, 14.13, 6.22; 251/212; 396/493, 505; 359/227, 230–232, 739

See application file for complete search history.

(56) References Cited

U.S. PATENT DOCUMENTS

| | | | | |
|---|---|---|---|---|
| 2003/0139808 A1* | 7/2003 | Shahinpoor et al. | ........... | 623/4.1 |
| 2004/0092922 A1* | 5/2004 | Kadziauskas et al. | .......... | 606/27 |
| 2005/0033202 A1* | 2/2005 | Chow et al. | ..................... | 601/46 |
| 2005/0234537 A1* | 10/2005 | Edin | ............................ | 623/1.11 |
| 2007/0030573 A1* | 2/2007 | Batchko et al. | ............... | 359/665 |

* cited by examiner

*Primary Examiner* — Corrine M McDermott
*Assistant Examiner* — Megan Wolf
(74) *Attorney, Agent, or Firm* — WPAT, P.C.; Anthony King

(57) ABSTRACT

An artificial sphincter system having: (1) a hollow object, which has the ability of contraction and expansion; (2) a shape memory alloy (SMA), which is connected with the hollow object, changes its shape to imitate the motion of human muscle by applying different electric current; (3) an electric power to provide different amounts of electric current to the shape memory alloy and let it contract or expand to control the motion of the hollow object to imitate the motion of human muscle; and (4) a photo resistor added between the electric power and the shape memory alloy, which senses the brightness of surrounding light and controls A/D (analog-to-digital) values of the electric power to cause different conditions of contraction and expansion of each part of the shape memory alloy.

16 Claims, 5 Drawing Sheets

Figure 3

| Voltage(V) | A/D Value | Parts of shape memory alloy | Condition of diaphragm | Brightness |
|---|---|---|---|---|
| ≦1.17 | ≦59 | 0 | Fully closed | High |
| 1.18~1.56 | 60~79 | 1 | | |
| 1.57~2.21 | 80~99 | 2 | | |
| 2.22~2.34 | 100~119 | 3 | | |
| 2.35~2.74 | 120~139 | 4 | | |
| 2.75~3.13 | 140~159 | 5 | | |
| 3.14~3.52 | 160~179 | 6 | | |
| 3.53~3.91 | 180~199 | 7 | | |
| ≧3.92 | ≧200 | 8 | Fully opened | low |

ARTIFICIAL SPHINCTER SYSTEM

FIELD OF THE INVENTION

The present invention relates to an artificial sphincter system, which can imitate the motion of human sphincter. In the preferred embodiment, the artificial sphincter system of the present invention is applied to imitate human iris, and it also can be used in a human body, a robot or a machine.

BACKGROUND OF THE INVENTION

Artificial iris implants are designed to replace missing or defective irises in human eyes either because the patient was born without an iris (a condition called aniridia) or suffered an injury or surgical damage to the iris.

The iris is the colored part of the eye that determines eye color and surrounds the pupil, the hole in the center of the iris that controls the amount of light entering the eye. Absence of the iris would cause poor vision and very severe sensitivity to light. Implantation of artificial iris benefits patients by allowing better light modulation into the eye and thereby improving vision and comfort.

The first artificial iris implant applied in US FDA clinical trial for iris implantation was manufactured by Ophtec USA, a Dutch BV in Groningen in the Netherlands with offices in the US. The clinical trial was carried out mainly by Kenneth J. Rosenthal, an attending ophthalmologist, in Great Neck, N.Y.

Artificial irises have been used in Europe, Canada, the Middle East and Asia, but rarely in the United States because the disease, aniridia, is a rare disorder, affecting only about 1 out of every 50,000 people. Another similar device, called the Rasch-Rosenthal Iris Diaphragm Ring, was co-invented by Dr. Rosenthal and Dr. Volker Rasch of Potsdam Germany in 1996. Then with Dr. Rasch's assistance, Dr. Rosenthal became the world's first surgeon who accomplished the human artificial iris implantation surgery in July 1996.

However, these prior arts still have many disadvantages. First, it takes large space in the eye to implant artificial iris hence may cause other eye disease after implantation. Second, the artificial iris made of acrylic material is fragile and therefore may be broken in the eye and then cause damage during impact. The last but not the least, the main function of most prior arts is to make one to be pleasing to the eye instead of physical function. Most of the prior arts can not control the amount of light entering the eyes.

SUMMARY OF THE INVENTION

The present invention provides a kind of artificial sphincter system comprising:
(1) a hollow object, which has the ability of contraction and expansion;
(2) a shape memory alloy, which is connected with the hollow object, changes its shape to imitate the motion of human muscle by applying different electric current;
(3) an electric power to provide different amounts of electric current to the shape memory alloy and let it contract or expand to control the motion of the hollow object to imitate the motion of human muscle; and
(4) a photo resistor added between the electric power and the shape memory alloy, which senses the brightness of surrounding light and controls A/D (analog-to-digital) values of the electric power to cause different conditions of contraction and expansion of each part of the shape memory alloy.

DETAILED DESCRIPTION OF THE INVENTION

The three main types of shape memory alloys (50) are the copper-zinc-aluminum-nickel, copper-aluminum-nickel, and nickel-titanium (NiTi) alloys. NiTi alloys are generally more expensive and to change from austenite to martensite upon cooling; Mf is the temperature at which the transition is finished. Accordingly, As and Af are the temperatures at which the reverse transformation from that repeated use of the shape memory effect may lead to a shift of the characteristic transformation temperatures (this effect is known as functional fatigue, as it is closely related with a change of microstructural and functional properties of the material).

The transition from the martensite phase to the austenite phase is only dependent on temperature and stress, not time, as most phase changes are, as there is no diffusion involved. Similarly, the austenite structure gets its name from steel alloys of a similar structure. It is the reversible diffusionless transition between these two phases that allow the special properties to arise. While martensite can be formed from austenite by rapidly cooling carbon-steel, this process is not reversible, so steel does not have shape memory properties.

The shape memory alloy (50) will change its shape or contract while meeting heat or an electric current which can generate heat on the shape memory alloy and the changed shape will recover to the original shape after blocking the electric current or the heat. This characteristic is applied to the artificial sphincter system of the present invention, and moreover, it can imitate iris when working with a diaphragm.

The present invention provides a kind of artificial sphincter system comprising:
(1) a hollow object (60), which has the ability of contraction and expansion; and
(2) a shape memory alloy (50), which is connected with the hollow object, changes its shape to imitate the motion of human muscle by applying different electric current.

The present invention further comprises an electric power (10) which provides different amounts of electric current to the shape memory alloy and lets it contract or expand to control the motion of the hollow object (60) to imitate the motion of human muscle. In the preferred embodiment, the present invention is activated by solar power. In the general embodiment, the voltage of the electric power is between 0~10 volts; in the preferred embodiment, the voltage of the electric power is between 0~7.5 volts; in the best embodiment, the voltage of the electric power is between 0~5 volts. The voltage signal is a kind of analog signal and is converted to a digital value, the A/D (analog-to-digital) value, for computer processing. The relationship between the voltage and the A/D value is shown in the first two columns of FIG. 3. In the general embodiment, the A/D value (the analog-to-digital value) of the electric power is between 0~300; in the preferred embodiment, the A/D value of the electric power is between 0~275; in the best embodiment, the A/D value of the electric power is between 0~255.

In a preferred embodiment, the hollow object (60) of the present invention is a diaphragm, which is controlled by the shape memory alloy and imitates the motion of human muscle by contraction and expansion. In the preferred embodiment, the artificial sphincter system is used to imitate an iris. In the artificial sphincter system of the present invention, a photo resistor (20) is added between the electric power and the shape memory alloy to control the electric current entering the shape memory alloy by sensing the brightness of surrounding light.

In the embodiment of iris imitation, the minimal force for moving the diaphragm is 12 g, and the force for opening the diaphragm to the maximum is 20 g. When associated with the photo resistor, the brightness of surrounding light that let the diaphragm open minimally is between 255~300 μW. In the embodiment of improving the similarity between the present invention and the human muscle, the shape memory alloy is divided into 4~12 parts; in the preferred embodiment, the shape memory alloy is divided into 6~10 parts; in the best embodiment, the shape memory alloy is divided into 8 parts.

The main function of most of the general artificial irises is to make one to be pleasing to the eye instead of physical function. Most of them can neither control the amount of light entering the eyes nor contract or expand. Comparing to the prior arts, the artificial sphincter system of the present invention have the contraction and expansion function and can be used in a human body, a robot or a machine.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

BRIEF DESCRIPTION OF THE DRAWINGS

The number of element is as follows:
10: electric power
20: photo resistor
30: circuit board
40: connecting cable
50: shape memory alloy
60: hollow object

FIG. 3 shows the contraction and expansion control of the shape memory alloy of the artificial iris of the present invention.

EXAMPLES

The example of the present invention was for imitating a human iris, so the hollow object in the example was replaced by a diaphragm.

1. Manufacture of the Artificial Iris System

Figure 1:
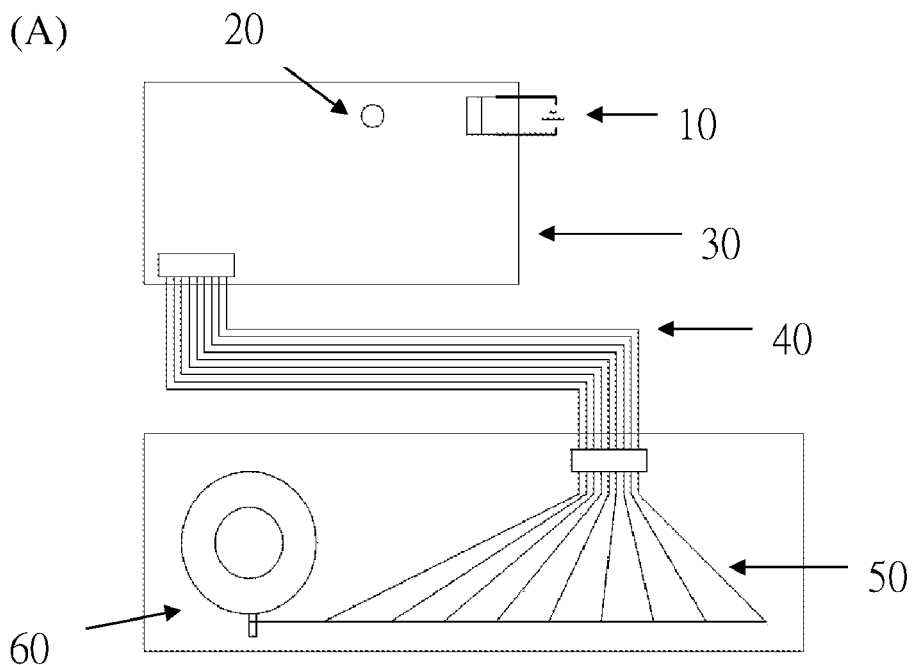
FIG. 1 shows (A) the virtual image and (B) the real image of the embodiment of the artificial iris.
Figure 1:
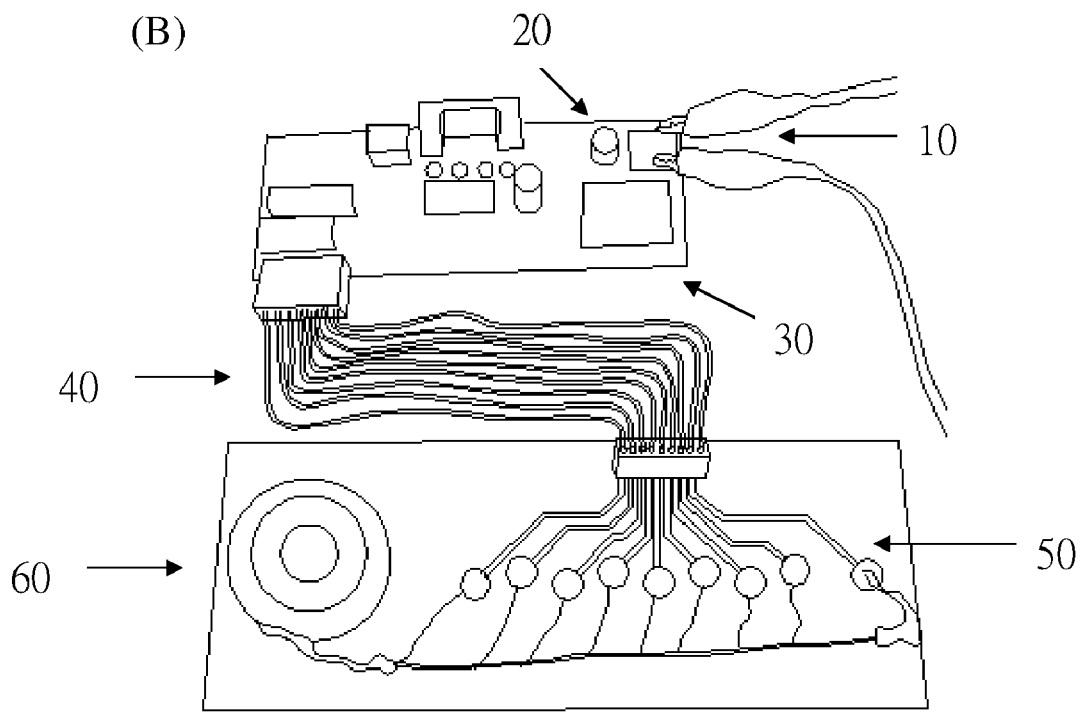

As shown in FIG. 1, combining the shape memory alloy and the diaphragm, making the partially electrified circuit of the shape memory alloy, sensing the brightness of the surrounding light by the photo resistor (20) on the circuit board (30), connecting with 10 volts DC power, and connecting the circuit board and the shape memory alloy by the connecting cable (40), the artificial iris system was completed.

2. The Mechanism of the Artificial Iris System

Figure 2:
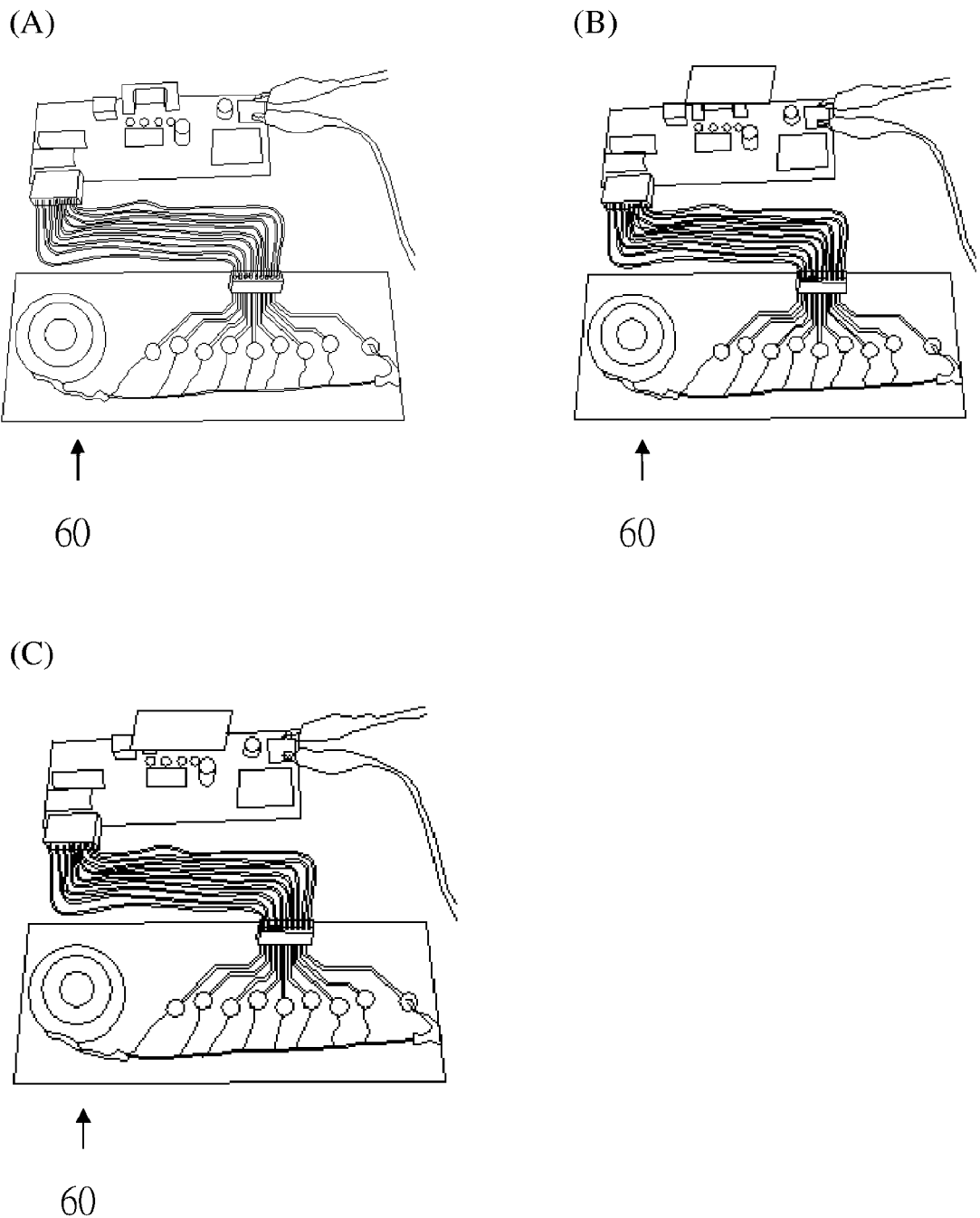
FIG. 2 shows the opening and closing condition of the artificial iris of the present invention with (A) high brightness; (B) low brightness (the paper covered half of the photo resistor); and (C) lower brightness (the paper covered most of the photo resistor).

The artificial iris system controlled the opening of the diaphragm through sensing the brightness of the surrounding light by the photo resistor (20), and then controlled the amount of electric current passing the shape memory alloy (50). The shape memory alloy would cause the opening or closing of the diaphragm by contraction and expansion. In the high brightness surrounding, there was no electric current passing the shape memory alloy, and the diaphragm would maintain in the minimal opening condition avoiding the strong light entering into the eyes; in the low brightness surrounding, there was a little electric current passing the shape memory alloy, and the diaphragm would be slightly opened; in the lower brightness surrounding, there was much electric current passing the shape memory alloy, and the diaphragm would be opened to the maximum (as shown in FIG. 2). The device regulated the amount of the light entering eyes as human iris.

3. The Condition of Contraction and Expansion of Each Part of the Shape Memory Alloy The shape memory alloy which controlled the contraction and expansion of the artificial iris of the present invention was divided into 8 parts. When adopting different amounts of surrounding light, the resistance of the photo resistor (20) varied and adjusted the contraction and expansion of the shape memory alloy by changing the voltage. The voltage was controlled in 0~5 volts, and different voltage had different A/D (analog-to-digital) value. The A/D value was between 0~225, and different A/D values caused different conditions of the contraction and expansion of each part of the shape memory alloy. As shown in FIG. 3, the voltage and the A/D values were changed when the light faded. The more parts the shape memory alloy contracted, the more areas the diaphragm opened.

Figure 4:
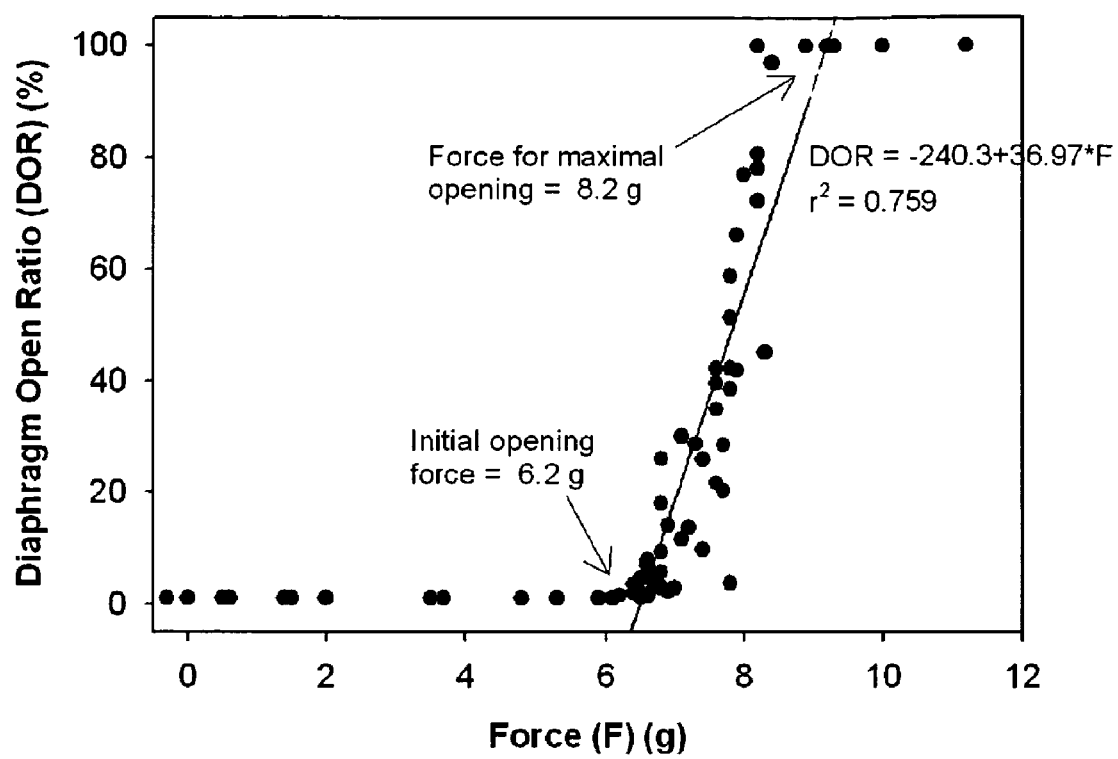
FIG. 4 shows the diagram of the relationship between the pulling force and the opening and closing condition (percentage) of the artificial iris of the present invention.

4. Test of the Relationship Between the Opening of the Artificial Iris System and the Pulling Force For measuring the force for opening and closing the artificial iris by a load cell, the examination steps were as follows:

First, the diaphragm was fixed, and the pulling direction of the diaphragm pole was matched with the motivating direction of the load cell. Second, the pole was pulled to make the diaphragm open to a certain degree by the load cell, and the pulling force was tested for 100 times. Finally, a diagram of the opening degree (percentage) versus the force measured by the load cell was drawn and the result was shown in FIG. 4. It needed 12 grams to motivate the diaphragm, and the measured force was gradually increased when the diaphragm was opening. As shown in FIG. 4, the force to arrive in the maximal opening condition of the diaphragm in this example was 20 grams.

Figure 5:
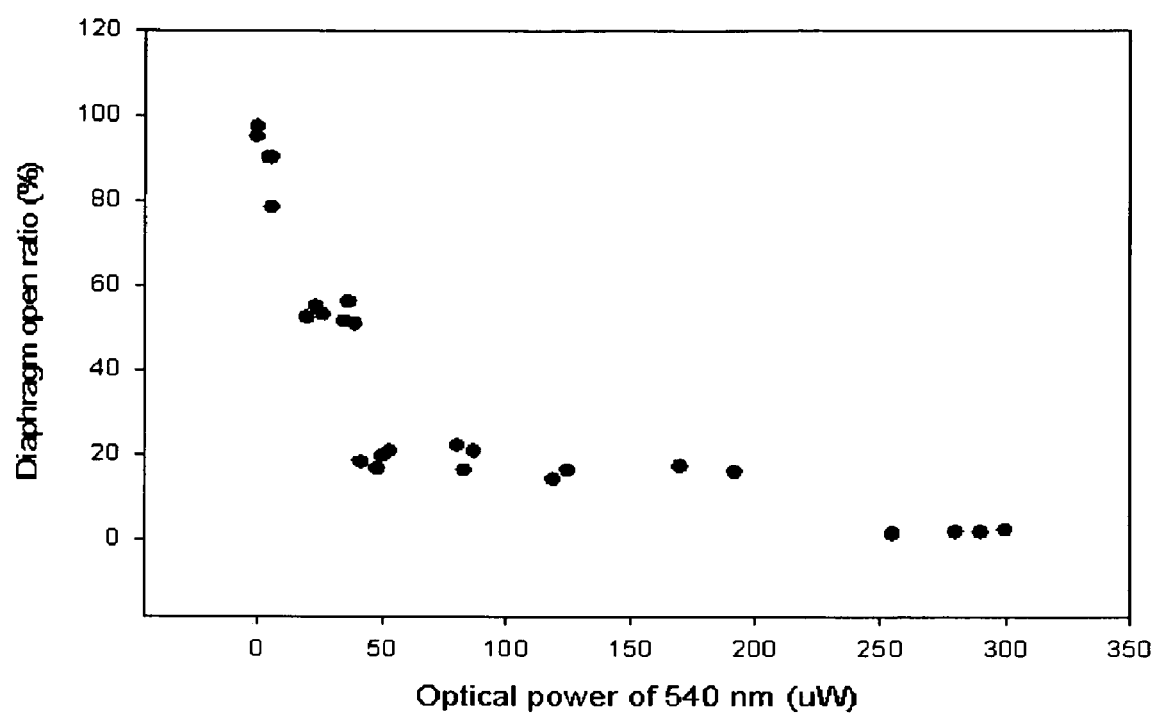
FIG. 5 shows the diagram of the relationship between the 540 nm optical power and the opening and closing condition of the artificial iris of the present invention (test for 26 times).

5. Test of the Relationship Between the Opening of the Artificial Iris System and Brightness of Surrounding Light For determining the relationship between the opening of the artificial iris system and brightness of surrounding light by a 540 nm light source (the peak absorbance wavelength of the photo resistor), the examination steps were as follows:

First, the photo resistor of the artificial iris was put under a 540 nm light source, and the other parts were wrapped in a mask to prevent the interference of outside light. Second, different light intensity was used to trigger different opening degree of the diaphragm and data were collected. Finally, the optical power under the same light intensity was measured by a photometer for 26 times, and a diagram of the opening degree of the diaphragm (percentage) versus the optical power of 540 nm was drawn, as shown in FIG. 5. The artificial iris was gradually closing when the optical power was increasing, and the diaphragm opened minimally when the optical power was between 255~300 μW (FIG. 5).

What is claimed is:

1. An artificial sphincter system comprising:
   (1) a hollow object, which has the ability of contraction and expansion;
   (2) a shape memory alloy, which is connected with the hollow object, which changes its shape to imitate the motion of human muscle when different amounts of electric current are applied;
   (3) an electric power to provide different amounts of electric current to the shape memory alloy to cause the shape memory alloy to contract or expand to control the motion of the hollow object to imitate the motion of human muscle; and
   (4) a photo resistor added between the electric power and the shape memory alloy, which senses the brightness of surrounding light and controls A/D (analog-to-digital) values of the electric power to cause different conditions of contraction and expansion of the shape memory alloy.

2. The artificial sphincter system of claim 1, wherein the hollow object is a diaphragm.

3. The artificial sphincter system of claim 2, wherein the diaphragm is used to imitate the motion of an iris.

4. The artificial sphincter system of claim 2, wherein the diaphragm is controlled by the shape memory alloy.

5. The artificial sphincter system of claim 2, wherein the brightness of surrounding light that causes the diaphragm to open minimally is between 255~300 μW.

6. The artificial sphincter system of claim 1, wherein the shape memory alloy is divided into 4~12 parts to improve the similarity between the artificial sphincter system and human muscle.

7. The artificial sphincter system of claim 6, wherein the shape memory alloy is divided into 6~10 parts to improve the similarity between the artificial sphincter system and human muscle.

8. The artificial sphincter system of claim 7, wherein the shape memory alloy is divided into 8 parts to improve the similarity between the artificial sphincter system and human muscle.

9. The artificial sphincter system of claim 1, wherein the voltage of the electric power is between 0~10 volts.

10. The artificial sphincter system of claim 9, wherein the voltage of the electric power is between 0~7.5 volts.

11. The artificial sphincter system of claim 10, wherein the voltage of the electric power is between 0~5 volts.

12. The artificial sphincter system of claim 1, wherein the A/D value of the electric power is between 0~300.

13. The artificial sphincter system of claim 12, wherein the A/D value of the electric power is between 0~275.

14. The artificial sphincter system of claim 13, wherein the A/D value of the electric power is between 0~255.

15. The artificial sphincter system of claim 1, which is activated by solar power.

16. The artificial sphincter system of claim 1, which is used in a human body, a robot or a machine.

* * * * *